US005549632A

United States Patent [19]
Lai

[11] Patent Number: 5,549,632
[45] Date of Patent: Aug. 27, 1996

[54] METHOD AND APPARATUS FOR OPHTHALMIC SURGERY

[75] Inventor: Shui T. Lai, Encinitas, Calif.

[73] Assignee: Novatec Laser Systems, Inc., Carlsbad, Calif.

[21] Appl. No.: 967,253

[22] Filed: Oct. 26, 1992

[51] Int. Cl.⁶ ............................................. A61B 17/36
[52] U.S. Cl. ............................. 606/5; 606/4; 606/10
[58] Field of Search ............................ 606/4, 5, 6, 19, 606/10, 11, 12, 15

[56] References Cited

U.S. PATENT DOCUMENTS

| | | | |
|---|---|---|---|
| 4,903,695 | 2/1990 | Warner et al. | 606/4 |
| 4,994,058 | 2/1991 | Raven et al. | 606/5 |
| 5,196,027 | 3/1993 | Thompson et al. | 606/5 |
| 5,336,215 | 8/1994 | Hsueh et al. | 606/4 |

FOREIGN PATENT DOCUMENTS

| | | | |
|---|---|---|---|
| 0372127 | 6/1990 | European Pat. Off. | 606/4 |
| 0006519 | 7/1989 | WIPO | 606/5 |

*Primary Examiner*—Angela D. Sykes
*Assistant Examiner*—Sonya Harris-Ogugua
*Attorney, Agent, or Firm*—Baker, Maxham, Jester & Meador

[57] ABSTRACT

A method and apparatus for precisely controlling and determining the location of the interaction point of a surgical laser beam, and for controlling the shape of the cornea during ophthalmic surgery. A transparent applanator plate is placed in contact with the cornea of a patient's eye. The applanator plate creates a fixed positional frame of reference from which a laser beam control system can determine the desired point or points at which to focus the surgical laser beam. A surgical tip at the distal end of an articulated arm having flexible joints is placed in contact with the applanator plate and follows any motion of the patient's eye and directs the laser beam to the surgical tip. The applanator plate also provides a means to control the contour of the index of refraction boundary between the corneal epithelium of the patient's eye and the air.

61 Claims, 12 Drawing Sheets

METHOD AND APPARATUS FOR OPHTHALMIC SURGERY

BACKGROUND OF THE INVENTION

1. Field of the Invention

This invention relates to a method and apparatus for performing ophthalmic surgery, and more particularly to a method and apparatus for performing ophthalmic surgery using a guided laser beam.

2. Description of Related Art

The use of laser beams to surgically alter the human eye is well known today, and is based upon the concept of correcting refractive errors by changing the curvature of the eye. This concept was brought forth early on, as illustrated in the notable mechanical methods pioneered by J. Barraquer. These mechanical procedures involve removal of a thin layer of tissue from the cornea by a micro-keratome, freezing the tissue at the temperature of liquid nitrogen, and re-shaping the tissue in a specially designed lathe. The thin layer of tissue is then re-attached to the eye by suture. The drawback of these methods is the lack of reproducibility and hence poor predictability of surgical results.

With the advent of lasers, various methods for the correction of refractive errors have been attempted, making use of the coherent radiation properties of lasers and the relative precision of the laser-tissue interaction. Peyman, et al., in Ophthalmic Surgery, vol. 11, pp. 325–9, 1980, reported that laser burns of various intensity, location, and pattern were produced on rabbit corneas. More recently, Horn, et al., in the Journal of Cataract Refractive Surgery, vol. 16, pp. 611–6, 1990, reported that a curvature change in rabbit corneas had been achieved with a laser by applying specific treatment patterns and laser parameters.

In U.S. Pat. No. 4,907,586 to Bille et al., a technique for tissue ablation of the cornea is disclosed in which a laser beam is focussed into a small volume of about 25–30 microns in diameter. The peak beam intensity at the laser focal point could reach about $10^{12}$ watts per cm$^2$. At such a peak power level, tissue molecules are "pulled" apart under the strong electric field of the laser light, which causes dielectric breakdown of the material. The conditions of dielectric breakdown and its applications in ophthalmic surgery have been described in the book "YAG Laser Ophthalmic Microsurgery" by Trokel. Bille et al. further discloses that the preferred method of removing tissue is to move the focused point of the surgical beam across the tissue. Near the threshold of the dielectric breakdown, the laser beam energy absorption characteristics of the tissue changes from highly transparent to strongly absorbent. The reaction is very violent, and the effects are widely variable. The amount of tissue removed is a highly non-linear function of the incident beam power. Hence, the tissue removal rate is difficult to control.

Additionally, while the technique might be useful for creating incisions within the stroma without disruption of the epithelium, Bowman's layer, or endothelium, such a procedure requires extremely precise control of the point at which the laser beam interacts with the tissue. Without such precise control, use of the procedure risks accidental exposure of the endothelium to the laser beam, and thus permanent damage to the eye. Bille fails to disclose a means by which the laser may be accurately and precisely controlled to affect only the desired tissue in the precise manner necessary for the success of such a procedure.

Currently, two methods are known by which a laser beam can be directed to specific points within the eye. One method involves manually directing a hand-held contact probe such as described in a paper entitled "Optically coupled technique for photorefractive surgery of the cornea" by J. Taboada and R. H. Poirier (*Optics Letters,* Vol. 15, No. 9, May 1990). Laser radiation capable of tissue photodisruption is delivered to ablate tissue within the stroma. The laser beam is delivered by means of a microscopic objective handpiece at the end of a low-inertia air-bearing-supported delivery arm. The handpiece comprises a pencil-like contact probe having objective lenses. Both lenses are plano-convex sapphire lens, with the plano side of the distal lens in contact with the corneal epithelium. The lenses function together to focus the laser beam. The physician directs the handpiece to a specified point and activates the laser. The contact probe is then repositioned and once again the laser is activated. This point-by-point process is repeated until the desired affect is achieved (e.g., an incision is created within the stroma). While this procedure provides a means to accurately affect the tissue within the stroma, it is limited in that the laser beam cannot be accurately controlled in the Z-axis (i.e., the depth of the interaction point is fixed). Moreover, control in the X and Y plane is limited by the inability of the surgeon to make straight cuts accurately by connecting contact points. Furthermore, the process is laborious and requires extraordinary care and control by the surgeon in positioning the contact probe.

The second method by which the laser beam may be directed to specific points within the eye involves automated control of the point at which the laser is focussed. In U.S. Pat. No. 4,718,418, L'Esperance, Jr. (the '418 patent), discloses the use of a scanning laser to achieve controlled ablative photodecomposition of one or more selected regions of a cornea. According to the disclosure, a laser beam is reduced in its cross-sectional area, through a combination of optical elements, to a 0.5 mm by 0.5 mm rounded-square beam spot that is scanned over a target by deflectable mirrors. To ablate a corneal tissue surface with such an arrangement, each laser pulse etches out a square patch of tissue. The patient's head is stabilized with respect to the laser by a clamping means. An eye-retaining fixture comprising a hollow annulus, having a convergent axial-end wall of air-permeable material contoured to engage and retain the eye via the scleral-corneal region, is fixed to the patient's eye to stabilize the position of the tissue to be affected by the laser with respect to the beam control apparatus. Each such square patch must be placed precisely adjacent to the next patch; otherwise, any slight displacement of any of the etched squares would result in grooves or pits in the tissue at the locations where the squares overlap and cause excessive erosion, and ridges or bumps of unetched tissue at the locations in the tissue where the squares are not contiguous. The resulting minimum surface roughness therefore will be about two times the etch depth per pulse. A larger etch depth of 14 microns per pulse is taught for the illustrated embodiment. This larger etch depth would be expected to result in an increase of the surface roughness, thus adversely affecting visual acuity.

If this type of system were used to ablate tissue within the stroma to try to preserve a smooth epithelium, there is a high risk the procedure would fail and damage would result to the epithelium, Bowman's layer, or endothelium. This is because the typical depth of a cornea is 600 microns. Thus, even such motion of the cornea with respect to the laser source as is generated by the patient's pulse or respiration could cause the interaction point of the laser beam to unintentionally and harmfully disrupt tissue which must remain undisturbed, such as the endothelium. Furthermore, even though an eye-retaining fixture is fixed to the scleral-corneal region, and the retaining fixture has a flange which allows the eye retaining fixture to be secured to the laser, small amounts of motion of the eye retaining fixture relative to the laser source are possible. In addition, the fact that the patient's head and eye must be held absolutely motionless with respect to the laser source for the entire duration of the operation places a strain on the patient.

In response to this need to more accurately determine and control the location of the point of interaction between the laser beam and the tissue to be affected, eye tracking systems have been contemplated which track the motion of the eye with respect to the source of the laser beam. Positional feedback indicative of corneal motion relative to the laser source would be used by the laser beam control system to compensate for motion of the eye with respect to the laser beam source. Clearly, such a tracking system is complex, expensive, and poses reliability concerns.

In addition to the problem of locating the interaction point of the laser beam relative to the tissue to be affected, the laser beam control system must precisely control the movement of the interaction point of the laser beam in three dimensions in order to create incisions that follow the contour of the cornea, and to create incisions of varying depth. The requirement that the interaction point be controlled in three dimensions adds a level of complexity to the procedure.

A further problem is created by the fact that the curved surface of the cornea, in combination with the difference in the index of refraction between air and the stroma, causes the laser beam to become distorted as the laser beams passes through the boundary between air and the epithelium. This distortion can further complicate the control of the laser beam by shifting the focal point, and thus the interaction point of the laser beam.

Therefore, it would be desirable to have a method and apparatus which controls the location of the focal point of a laser beam, such that extremely accurate positioning of the interaction point of the laser with respect to the eye is possible, thereby permitting the safe use of a high power laser to affect the tissue within the stroma without risk of disrupting the epithelium, endothelium, or Bowman's layer. It would also be desirable for such a laser system to accommodate motion of the eye with respect to the laser beam source. Further, it would also be desirable to be able to controllably deform the corneal surface to improve and simplify certain types of surgical procedures. Furthermore, it would be desirable to have a method and apparatus which simplifies the laser beam control requirements such that two-dimensional control of the laser beam results in an incision which follows the contour of the cornea, or which deviates therefrom in a precise and controlled manner.

The present invention provides an ophthalmic surgical system which permit safe use of a high power laser beam to affect tissue within the stroma of a human eye. The present invention also accommodates motion of the patient's eye during the surgical procedure, while maintaining accurate location of the interaction point of the surgical laser beam. In addition, the present invention allows a three-dimensional incision to be made in the cornea of a patient's eye without the need to control the laser beam in more than two dimensions.

SUMMARY OF THE INVENTION

The present invention is a method and apparatus for precisely controlling and determining the location of the interaction point of a surgical laser beam, and for controlling the shape of the cornea during ophthalmic surgery. A transparent applanator plate is placed in contact with the cornea of a patient's eye. The applanator plate creates a fixed positional frame of reference from which a laser beam control system can determine the desired point or points at which to focus the surgical laser beam, and thereby direct an interaction point of the beam to very precisely defined locations within the patient's eye. The surface of the applanator plate in contact with the patient's eye can be planar, concave, or convex, with either a spheric or aspheric curvature, a compound curve, or any other shape chosen by the surgeon. Applying the applanator plate to the cornea of the patient's eye causes the cornea to conform to the shape of the applanator plate.

A surgical tip at the distal end of an articulated arm having flexible joints is placed in contact with the applanator plate and follows any motion of the patient's eye. The articulated arm is coupled to a surgical laser source including a laser beam control system, such as the system described in co-pending patent applications filed by the present inventor for inventions entitled "Two Dimensional Scanner-Amplifier Laser" (U.S. patent application Ser. No. 07/740,004), and "Method of, and Apparatus for, Surgery of the Cornea" (U.S. application Ser. No. 07/788,424). The surgical laser source also includes the source of the laser beam. The articulated arm directs the laser beam to the surgical tip, translating the motion of the beam relative to a reference frame fixed to the surgical laser source to a reference frame fixed with respect to the applanator plate to which the surgical tip is in contact. Since the shape of the cornea conforms to the surface contour of the applanator plate, incisions of various shapes can be made by selecting an appropriate applanator plate and controlling the surgical beam to move linearly with respect to the fixed frame by the applanator plate.

The applanator plate also provides a means to control the contour of the index of refraction boundary between the corneal epithelium of the patient's eye and the air. Controlling the contour of this boundary reduces the distortion of the surgical laser beam which would otherwise be present due to the curvature of the outer surface of the epithelium and the difference in the index of refraction between the air and the stroma underlying the epithelium. The index of refraction of the applanator plate is preferably closely matched to the index of refraction of the cornea (i.e., index of approximately 1.38). The upper surface of the applanator plate is selectively shaped to provide a desirable contour at the boundary between the index of refraction of the stroma and air.

Thus, the applanator plate serves at least three purposes: (1) to provide a positional reference for a surgical laser; (2) to control the shape of the patient's cornea during a surgical laser procedure; and (3) to provide a boundary between the epithelium and air, the contour of which can be controlled to reduce the distortion of the surgical laser beam.

The details of the preferred embodiment of the present invention are set forth in the accompanying drawings and the description below. Once the details of the invention are known, numerous additional innovations and changes will become obvious to one skilled in the art.

BRIEF DESCRIPTION OF THE DRAWINGS

FIG. 2a is an illustration of an embodiment of the optical train through the articulated arm of the present invention.

FIG. 2b is an illustration of an embodiment of the present invention in which fiber optic guides the surgical laser beam to the surgical tip.

Like reference numbers and designations in the various drawings refer to like elements.

DETAILED DESCRIPTION OF THE INVENTION

Throughout this description, the preferred embodiment and examples shown should be considered as exemplars, rather than as limitations on the present invention.

Figure 1:
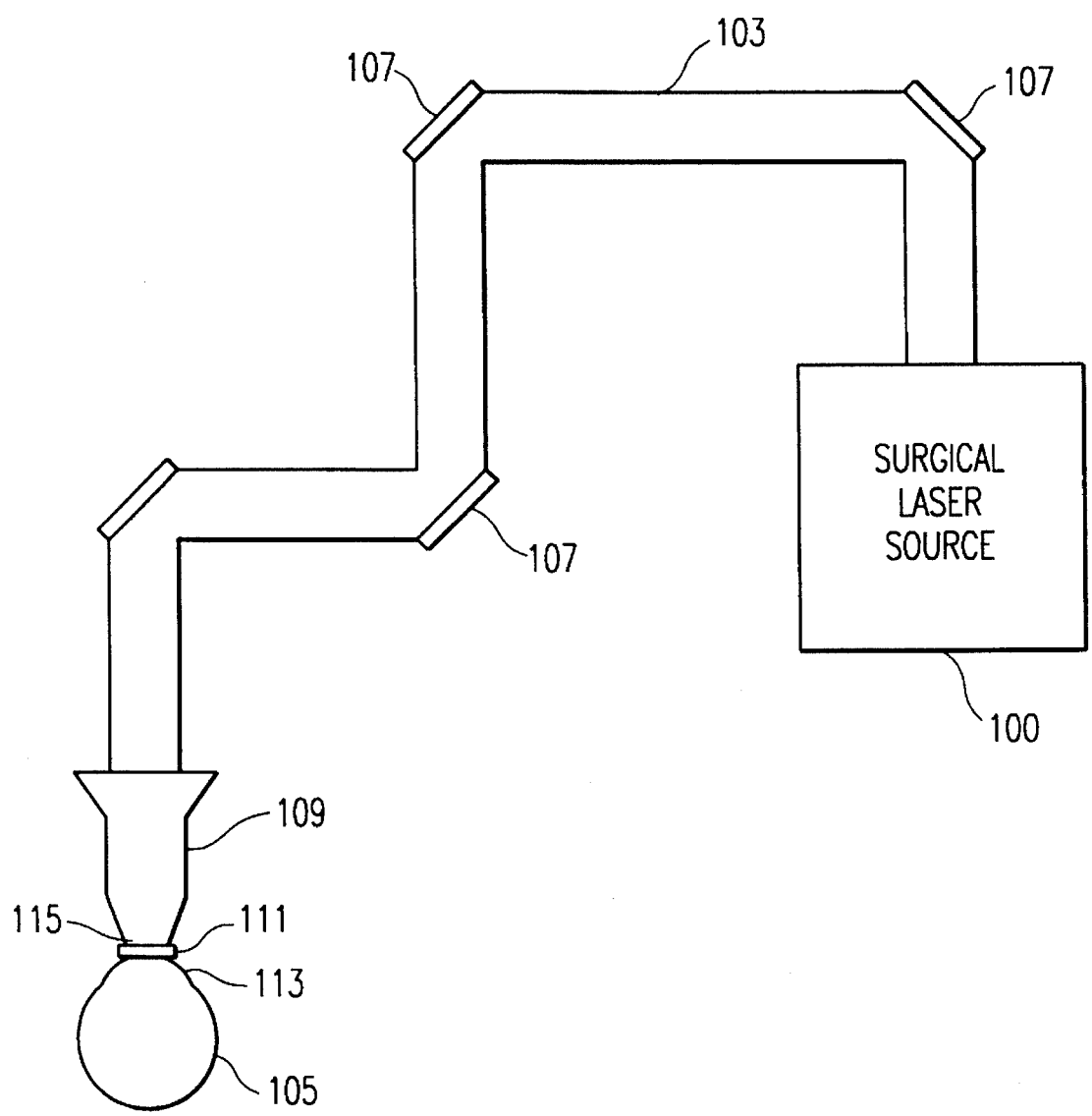
FIG. 1 is a front plane view of the preferred embodiment of the present invention.

FIG. 1 is an illustration of the preferred embodiment of the present invention. The preferred embodiment of the present invention comprises a surgical laser source 100 including a laser system (not shown), such as the system disclosed in a co-pending application for U.S. patent filed by the present inventor, entitled "Method of, and Apparatus for, Surgery of the Cornea" (U.S. application Ser. No. 07/788, 424), having a Ti-doped $Al_2O_3$ laser emitting pulses at about 100 to about 50,000 laser pulses per second. The laser beam is directed to an intended interaction point to be ablated by a laser beam control means, such as the type described in co-pending applications for U.S. patent filed by the present inventor for inventions entitled "Two Dimensional Scanner-Amplifier Laser" (U.S. patent application Ser. No. 07/740, 004), and "Method of, and Apparatus for, Surgery of the Cornea" (U.S. patent application Ser. No. 07/788,424). An articulated arm 103 having flexible joints 107 guides the laser beam from the surgical laser source to a surgical tip 109 along a path determined by the disposition of each flexible joint 107. In the preferred embodiment of the present invention, the distal end 115 of the surgical tip 109 is placed in contact with an applanator plate 111.

Figure 2:
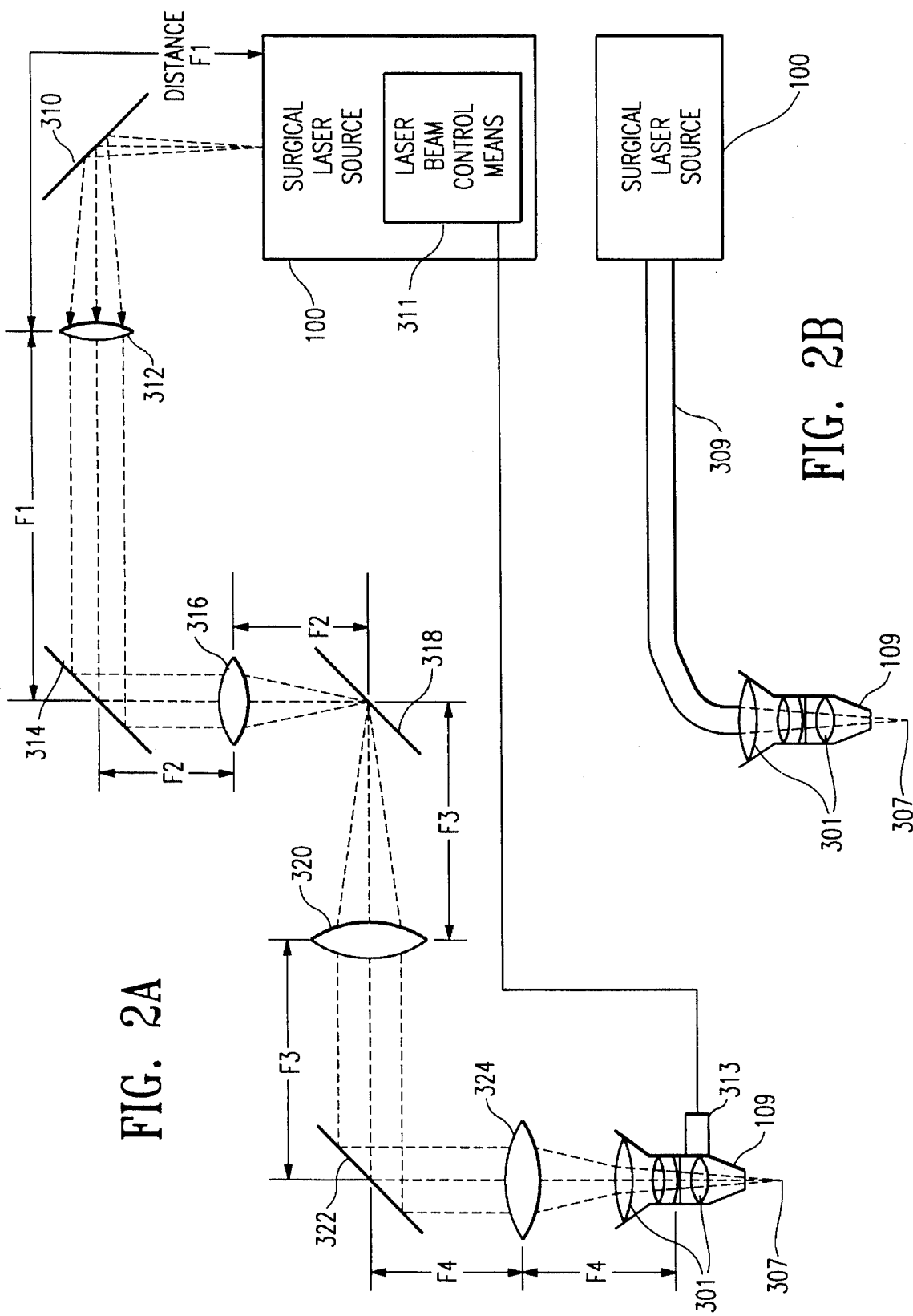
FIG. 2 is an illustration of one embodiment of the optical train through the articulated arm of the present invention.

The optical train through the articulated arm 103 is shown in detail in FIG. 2. In the illustrated embodiment, four lenses are used to control the beam diameter, within the cross-sectional area of the articulated arm 103 required to direct the surgical beam to each point of interest within the eye. The surgical beam is emitted by the surgical laser source 100 and is directed to strike a series of reflective surfaces, such as a polished mirror 310 located at the flexible joint 107, which redirect the beam to follow the path of the articulated arm 103. In the preferred embodiment, each flexible joint is capable of rotating about one axis of rotation. The beam is reflected off the first mirror 310 and passes through the first lens 312. The first lens 312 has a focal length of f1 and is positioned a distance of f1 from the laser source. Passing the beam through the first lens 312 prevents further divergence of the beam from the local longitudinal axis of the articulated arm 103.

After passing through the first lens 312, the beam propagates a distance f1 and strikes a second mirror 314 located at a second of the flexible joints 107 of the articulated arm 103. The second mirror 314 redirects the beam once again. After striking the second mirror 314, the beam continues propagating through the path of the articulated arm 103 a distance f2 to a second lens 316, having a focal length of f2. Upon passing through the second lens 316, the beam begins to converge toward the focal point of that lens a distance f2 ahead. The beam strikes a third mirror 318 located at a third flexible joint 107. The surface of the third mirror 318 is coincident with the focal point of the second lens 316. The third mirror 318 redirects the beam to continue down the path through the articulated arm 103. The beam diverges from the local longitudinal axis of the articulated arm 103 as it leaves the surface of the third mirror 318. A third lens 320 having a focal length of f3 is located at a distance f3 from the third mirror 318. The third lens 320 stops the beam from diverging further from the longitudinal axis of the articulated arm 103.

A fourth mirror 322 is located at a fourth flexible joint 107 a distance f3 from the lens 320. The beam reflects off the fourth mirror 322 and continues down the path of the articulated arm 103. A fourth lens 324 having a focal length f4 is located a distance f4 from the mirror 322. The fourth lens 324 causes the beam to converge toward the focal point located a distance f4 from the lens 324. The beam enters the surgical tip 109 at a distance which is less than the distance f4. Once the beam enters the surgical tip 109, the beam is finely focussed to a spot beam at the interaction point 307.

It can be seen from the above discussion and from FIG. 2 that the combination of lenses and mirrors of the articulated arm 103 provide a means by which points on a frame of reference fixed with respect to the laser source 100 can be mapped into a second frame of reference fixed with respect to the surgical tip 109 at the end of the relatively long and narrow articulated arm 103. It should be understood that the particular configuration of mirrors and lenses described herein is merely meant to be illustrative of the means by which the beam is directed to the surgical tip 109. Alternative embodiments in which the mirrors have curved surfaces and the number of optical elements vary from that illustrated are possible and remain within the scope of the present invention.

Figure 3:
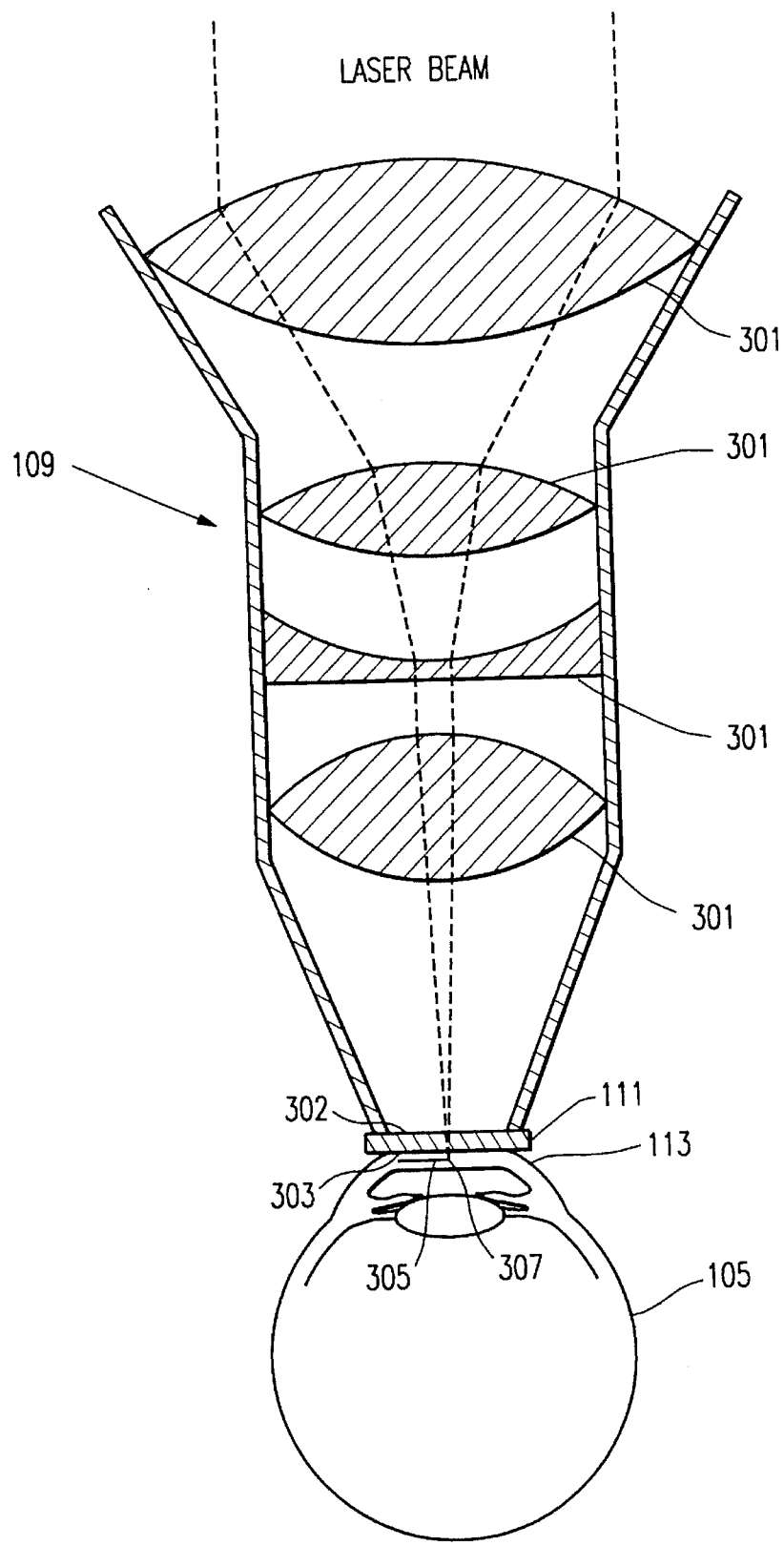
FIG. 3 is a cross-sectional side view of the surgical tip of the present invention in contact with an applanator plate in accordance with the present invention.

FIG. 3 is an illustration of the surgical tip 109 of the present invention which is in contact with an applanator plate 111 made and used in accordance with the present invention. The applanator plate 111 is in contact with the corneal epithelium 113 of a patient's eye 105. In the preferred embodiment, a wetting solution, such as a saline solution, is applied to enhance the contact between the applanator plate 111 and the eye 105. Optical focusing elements 301 are used to focus the interaction point of the surgical beam in known fashion. The applanator plate 111 is preferably constructed of a transparent light weight plastic, such as acrylic, having an index of refraction that closely matches that of a cornea (i.e., approximately 1.38).

Figure 4:
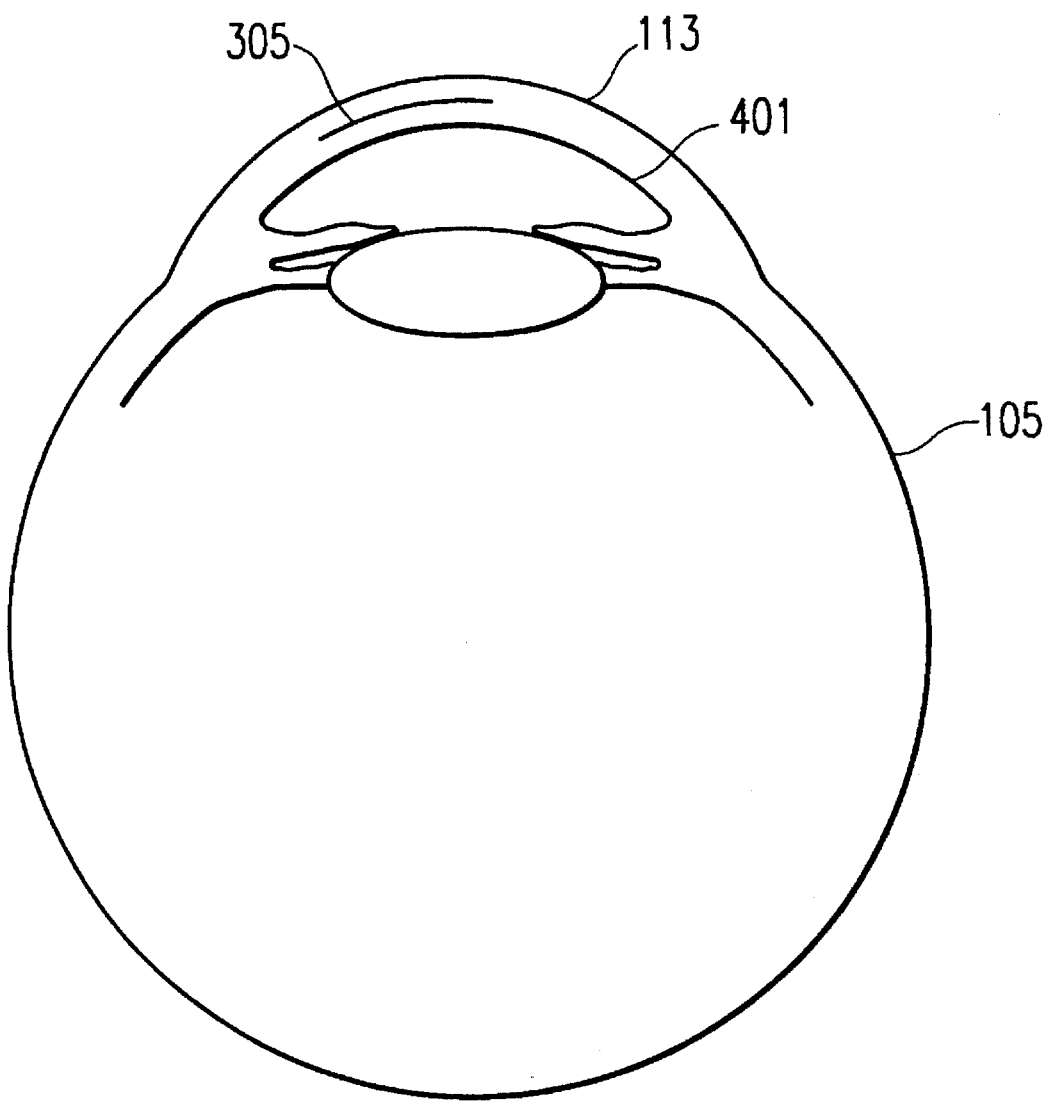
FIG. 4 is a cross-sectional side view of a resulting incision made by the present invention after removing the applanator plate from the corneal epithelium.
Figure 4A:
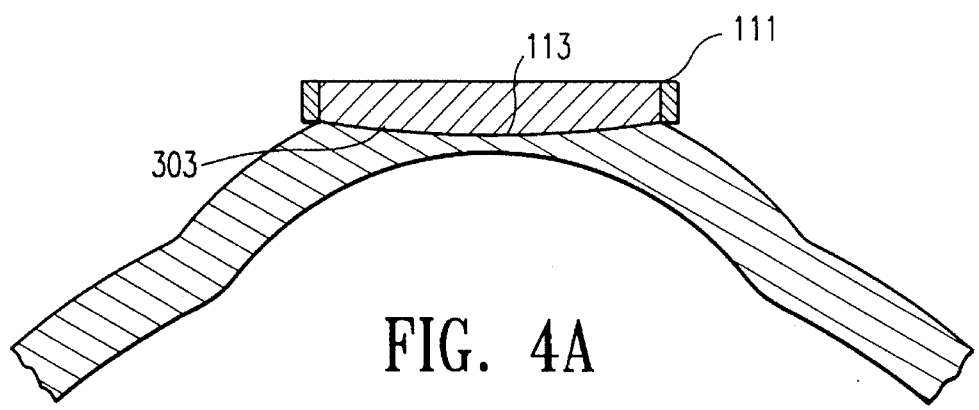
FIG. 4A is a cross-sectional side view of a convex applanator plate applied to an eye.
Figure 4B:
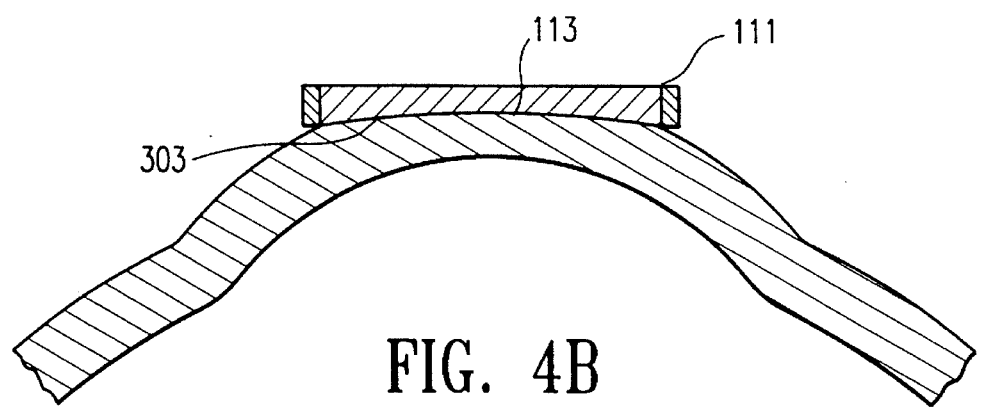
FIG. 4B is a cross-sectional side view of a concave applanator plate applied to an eye.

In the embodiment of the invention illustrated in FIG. 3, the applanator plate 111 has at least two planar surfaces, a tip surface 302 in contact with the surgical tip 109 and a corneal surface 303 in contact with epithelium 113. The applanator plate 111 is placed in contact with the corneal epithelium 113 and deforms the cornea to conform to the shape of the corneal surface 303. The corneal surface 303 of the applanator plate 111 may be shaped to conform the cornea to any contour that would be helpful in performing a particular surgical procedure. For example, the corneal surface 303 of the applanator plate 111 may be planar, convex or concave with a spheric or aspheric curvature, or may conform to any irregular shape that would be advantageous for the surgical procedure to be performed. For example, in FIGURE 4A, the applanator plate 111 may have a convex corneal surface 303 which deforms the cornea such that incisions may be made which are close to the epithelium at the center of the cornea, but which are further away from the epithelium toward the edges of the cornea. FIG. 4B shows an applanator plate 111 having a concave corneal surface 303 having a curvature that matches the curvature of the eye has the advantage of creating no beam distortion, and little or no corneal deformation. Furthermore in an alternative embodiment of the present invention, the corneal surface 303 may have a rough texture.

The area of contact between the applanator plate 111 and the cornea is preferably about 0.5 mm to 20 mm in diameter, as selected by a surgeon. The applanator plate 111 creates a prepared area on an eye for conducting a surgical procedure with a laser beam. By conforming the cornea to the shape of the corneal surface 303 of the applanator plate 111, a non-linear incision may be made by moving the beam linearly. Control of the surgical beam in a two-dimensional (X, Y) plane perpendicular to the longitudinal axis of the surgical tip 109 results in a three-dimensional incision. For example, the approximately lineal incision 305 shown in FIG. 3 was created by moving the surgical beam along a single axis. FIG. 4 illustrates the resulting incision 305 after removing the applanator plate 111 from the corneal epithelium 113. It can be seen from FIG. 4 that the resulting incision 305 follows the curvature of the surface of the epithelium 113. This greatly simplifies the control of the laser beam. In particular, the use of a plano-plano applanator plate 111 makes it possible to follow the contour of the surface of the epithelium 113 without complex apparatus to determine the contour thereof, or the need to control the beam in more than two dimensions.

Control of the interaction point of the laser beam in the Z-axis is accomplished by moving one or more lenses in the optical train (see FIG. 2) from the laser source to the last lens in the surgical tip 109. Such movement may be done manually or under automated control (for example, by a computer-controlled actuator such as a galvanometer drive). In the preferred embodiment of the present invention, the tip surface 302 of the applanator plate 111 is planar. This reduces the distortion that would otherwise occur as the laser beam crosses the boundary from the air above the applanator plate 111 into the applanator plate 111 due to the difference in the index of refraction between the air and the applanator plate 111. Since the applanator plate 111 preferably has an index of refraction close to that of the stroma of an eye, the curved boundary between the corneal surface 303 of the applanator plate 111 and the epithelium does not distort the surgical laser beam. In an alternative embodiment of the present invention, the contour of the tip surface 302 of the applanator plate 111 may be other than planar. For example, the surface may be either convex or concave, with a spheric or aspheric curvature, or may conform to any irregular shape that would be advantageous for the surgical procedure to be performed. A convex tip surface 302 can be used as a focusing element for the laser beam, allowing a small f number optics, and consequently a more tightly focused interaction point.

The applanator plate 111 provides a rigid reference point for the surgical tip 109 with respect to the eye 105. Therefore, very accurate work can be done with the laser beam without risk that the beam will accidentally contact the endothelium 401. This is critical, since any contact between the interaction point 307 of the laser beam and the endothelium 401 may cause permanent damage to the eye 105, as the endothelium 401 is vital for bringing nutrients to the eye 105 and does not regenerate in humans. (See FIG. 4). Importantly, flexibility of the articulated arm 103, and the connection between the surgical tip 109 at the distal end of the articulated arm 103, the applanator plate 111, and the eye 105 causes the distal end of the articulated arm 103 to precisely mechanically track the motion of the eye 105. Thus, a three-dimensional positional frame of reference that is fixed with respect to the distal end of the articulated arm 103 becomes fixed with respect to the applanator plate 111, and therefore with respect to the eye 105. This is important, because the eye is in near constant motion relative to all three axes due to the patient's pulse, breath, and reflexive impulses. Therefore, since the interaction point 307 of the beam is located with respect to the surgical tip 109, which is in contact with the applanator plate 111, and the applanator plate 111 is in contact with the epithelium 113, the entire eye 105 cannot move with respect to the reference used to guide the positioning of the interaction point 307.

In the preferred embodiment, a simple ultrasonic distance measuring apparatus, such as a pachymeter, can be used to determine the relative location of each of the relevant regions within the cornea, such as the endothelium, and Bowman's layer. This information permits a surgeon to focus the surgical beam with the optical focusing elements 301 to locate the interaction point 301 at a desired depth within the eye 105.

Figure 4C:
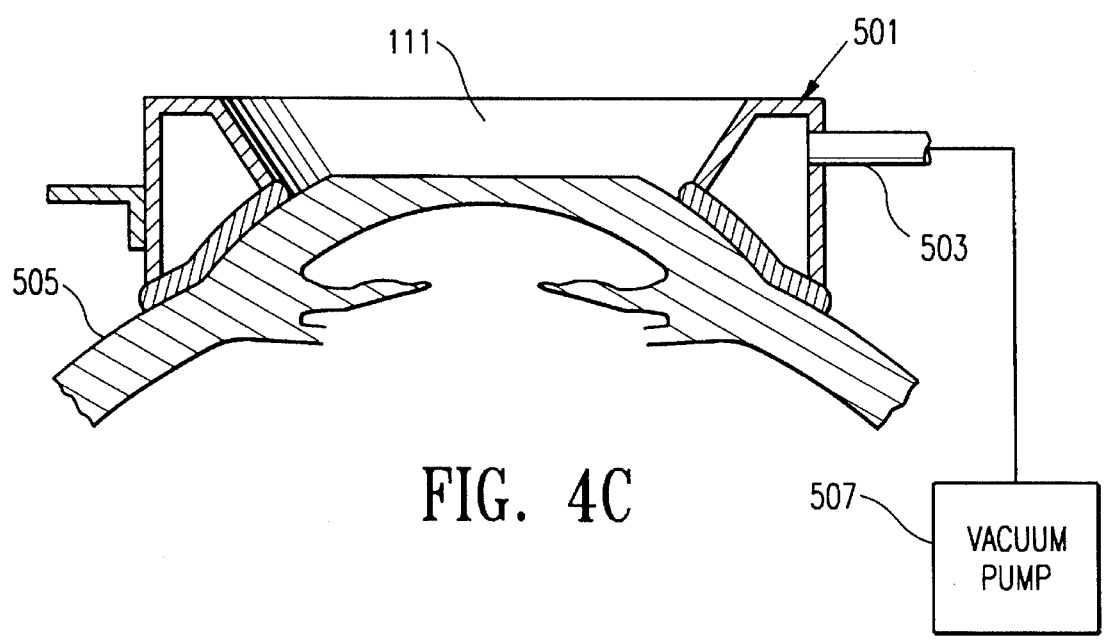
FIG. 4C is a cross-sectional side view of the use of a retention ring in accordance with the present invention.

In the preferred embodiment of the present invention, the applanator plate 111 may be secured to the eye by a retention ring attached to the scleral-corneal region of the eye. As is known, the retention ring may be held in place by partial vacuum pressure generated by a vacuum pump coupled to the retention ring. One such retention ring is shown in U.S. Pat. No. 4,718,418 to L'Esperance, Jr. FIG. 4C illustrates the use of a retention ring 501 in accordance with the present invention. Vacuum line 503 creates a vacuum pressure against the sclera 505, thereby preventing the applanator plate 111 from moving with respect to the eye 105.

Figure 5:
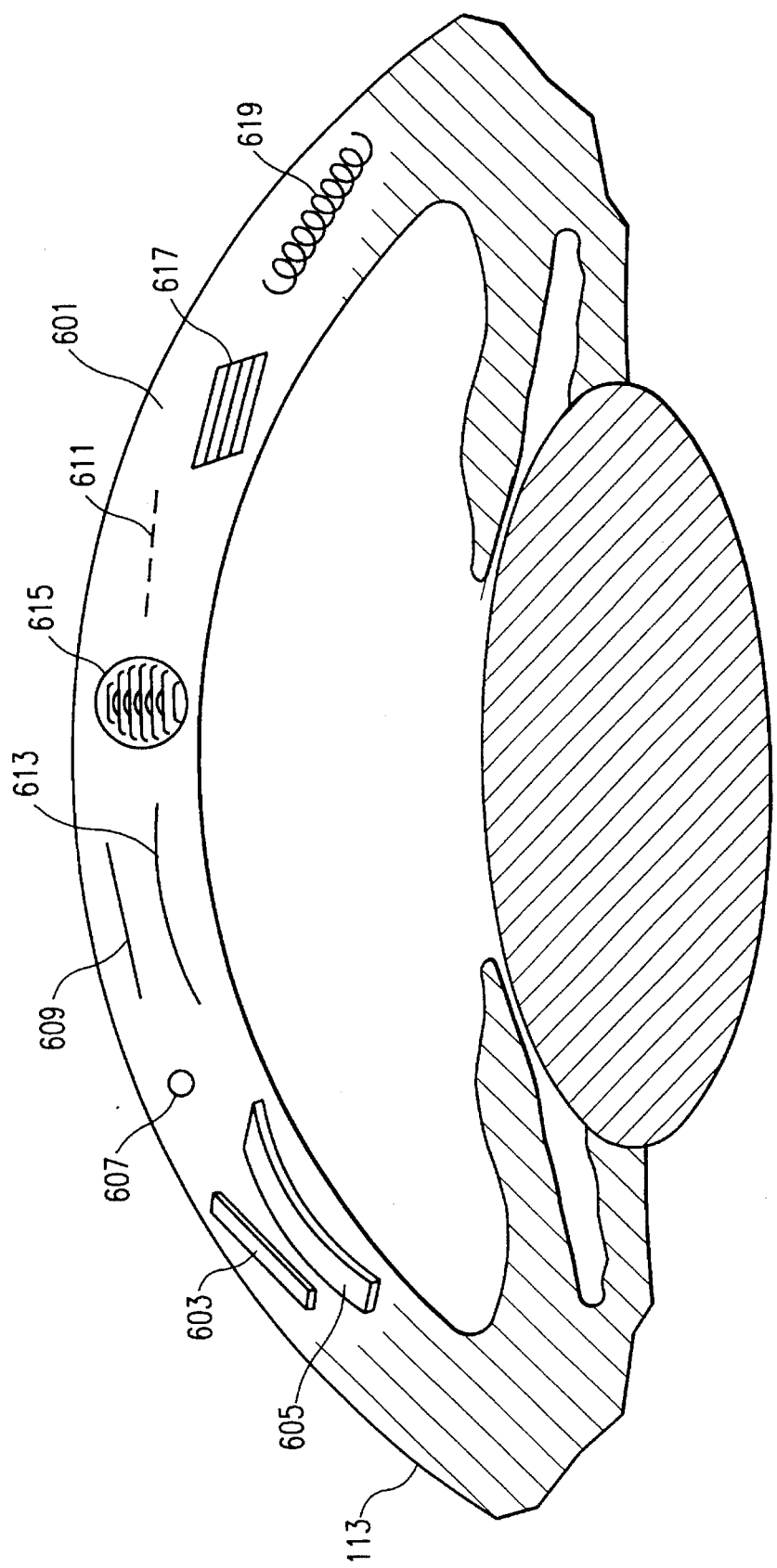
FIG. 5 is a cross-sectional side view of a cornea showing some of the resulting incisions which can be formed in a stroma by the present invention.

A major advantage of the present invention is the ease and accuracy with which interior portions of the stroma can be liquified, vaporized, or welded (i.e., heat melted). It is well known that incisions made within the stroma and which preserve the Bowman's layer and the epithelium have the advantages of (1) reduced pain, (2) faster healing, and (3) no post-operative haze. FIG. 5 illustrates some of the resulting incisions which can be formed in a stroma 601. The incisions shown in FIG. 5 are merely intended to illustrate a limited number of examples of the types of incisions that can be made using the invention, and is not intended to demonstrate any particular surgical procedure, or to imply that the illustrated incisions are the only relevant types of incisions that can be easily made in accordance with the present invention. The incisions illustrated in FIG. 5 include a straight channel 603, a curved channel 605, a point 607, a line 609, an interrupted line 611, a curve of varying depth 613, a circular area 615, a square or parallelepiped area 617, or a spiral 619. The invention encompasses any combination of such incisions. The laser may be either a continuous wave (CW) or pulsed (shuttered) laser. In an alternative embodiment of the present invention, the applanator plate 111 may be marked to aid in guiding the laser beam during the surgical procedure.

Applicable Surgical Procedures

The laser surgical system of the present invention can perform numerous types of surgical procedures on Bowman's layer, the stroma, anterior capsule, lens, posterior capsule, iris, vitreoretinal membranes, and the retina. Among other procedures, two types of laser tissue interaction are particularly suited for the inventive system:

(1) The inventive system can easily create straight line and curved-line excisions, of any predetermined length and depth, at a very precise location determined by a surgeon.

Figure 6:
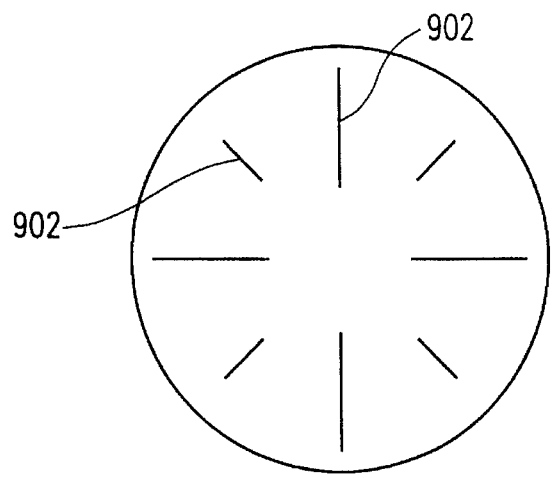
FIG. 6 is a top view of a cornea, showing the use of the present invention to make radial incisions on the cornea.

As illustrated in FIG. 6, multiple radial cuts 902, equal or partially equal in incision length and with an angular separation between cuts, can be made on the cornea with the present surgical system. An incision can be made by directing the surgical laser beam to a predetermined location at the cornea, and removing the desired amount of tissue by controlling the laser beam energy dosage. The incision may be made with either a wide incision width by using a larger beam spot size on the cornea surface, or a fine incision width by using a more focussed beam spot.

Figure 7A:
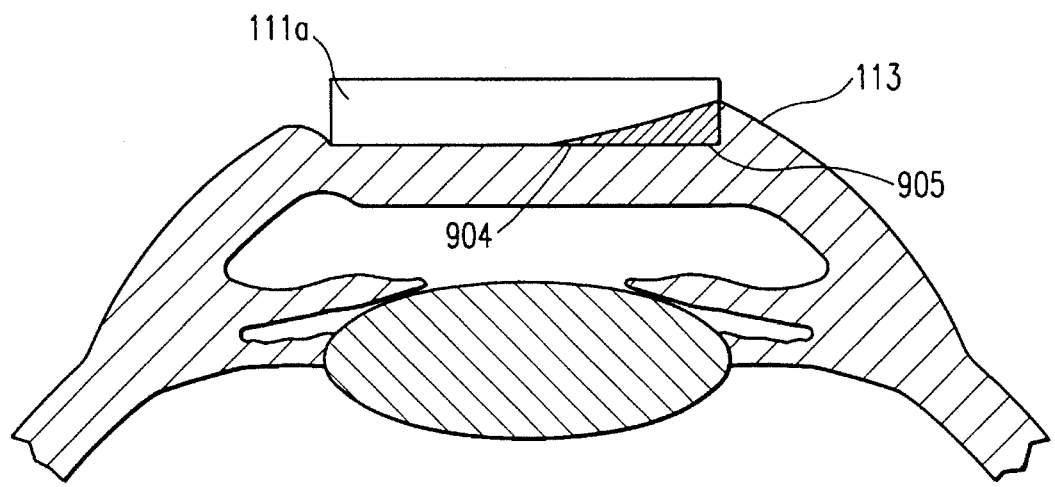
FIG. 7A is a cross-sectional side view of the use of a partially curved applanator plate used to create an incision of varying depth within a stroma in contact with a cornea.
Figure 7B:
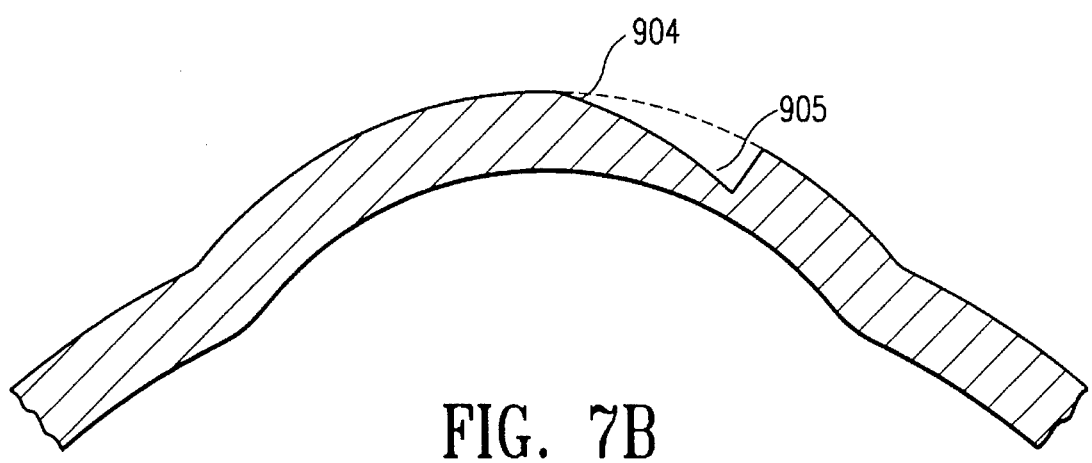
FIG. 7B is a cross-sectional side view of the cornea of FIG. 7A after the applanator plate has been removed, showing a shallower cut depth near the central region of the cornea and a deeper cut depth near the outer edge of the cornea.

With the present invention, the depth of each cut can be very accurately varied over the length of the cut, either by directly controlling the location and volume of the interaction point, or by varying the contour of the surface of the applanator plate 111a which is in contact with the epithelium 113, as shown in FIG. 7A. FIG. 7A illustrates an incision having a shallow portion 904 and a deep portion 905. Such an incision may be made entirely within the stroma without disruption of the epithelium, endothelium, or Bowman's layer. In FIG. 7B, a side view of a cross-section of the cornea after the applanator plate 111a has been removed shows a shallower cut depth 904 near the central region of the cornea and a deeper cut depth 905 near the outer edge of the cornea. Such a procedure provides more uniform stretching of the cornea from the central to the edge regions, and increases post-operative visual acuity.

Figure 8:
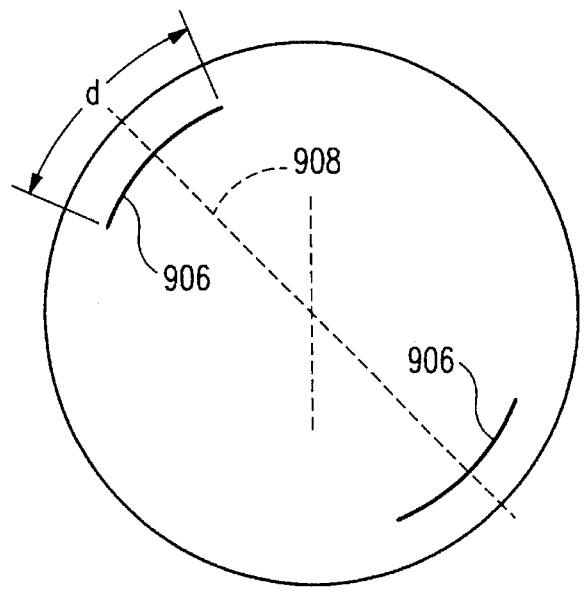
FIG. 8 is a top view of a cornea, showing the use of the present invention to make transverse-cut incisions on the cornea.

The invention can also easily generate transverse cuts ("T-cuts"), as shown in FIG. 8. By directing the surgical laser beam to make a pair of opposing transverse excisions 906 along an axis 908 relative to the center of the eye, the refractive power of the eye is decreased along the axis. The exact length d and the location of the incision can vary according to the amount of desired correction, in known fashion.

The inventive system can also be used for procedures in cornea transplants. A circumcision of the cornea in any predetermined shape (e.g., circular, elliptical, hexagonal, etc.) can be performed on the donor eye and the recipient's eye. In both cases, a computer control unit as described in the co-pending application for U.S. patent entitled "Method of, and Apparatus for, Surgery of the Cornea" (U.S. patent application Ser. No. 07/788,424), calculates the beam location based on the location of the applanator plate 111 relative to the location of the desired incision, the particular shape incision, and the amount of laser energy needed to cut through the cornea.

In general, excisions in the cornea can be made at effective locations for performing radial keratotomies or making T-cuts, to correct myopia, hyperopia, or astigmatism (regular or irregular).

(2) The second important type of laser-tissue interaction provided by the inventive system is area ablation, which permits direct sculpting of the corneal surface.

Figure 9:
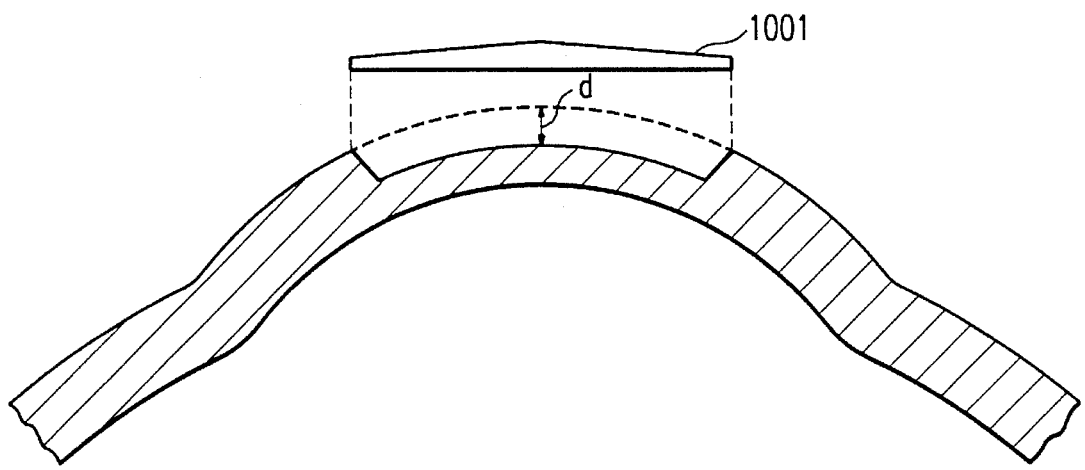
FIG. 9 is a cross-sectional side view of a cornea, showing the use of the present invention to remove tissue to a desired depth d over a predetermined area on the cornea, and showing an alternative method for performing a cornea transplant.

As illustrated in FIG. 9, a local scar or infected tissue can be removed with the present invention. The defective tissue is removed to a desired depth d over a predetermined area on the cornea. A donor cornea cap can be cut and ablated ("sculpted") to the desired dimension, curvature, and thickness using the invention described in co-pending U.S. patent application Ser. No. 07/788,424. The cap piece is then transferred to the bared stroma bed and attached by suture, glue, or other appropriate means, in known fashion. Such a cap can be used to change the refractive power of the eye to correct myopia, hyperopia, or astigmatism (regular or irregular).

Again referring to FIG. 9, an alternative method is shown for performing a cornea transplant. The invention can be used to ablate the cornea most of the way or all of the way through, from the epithelium to the endothelium of the cornea. Then a donor cornea 1001 is cut to matching dimensions, and attached to the open ablated area by sutures or other known methods.

Figure 10:
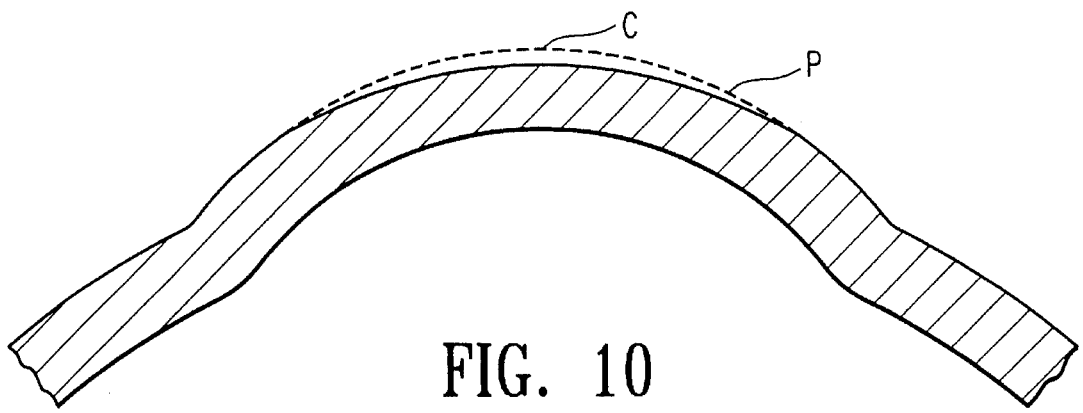
FIG. 10 is a cross-sectional side view of a cornea, showing the use of the present invention to correct myopia.
Figure 10A:
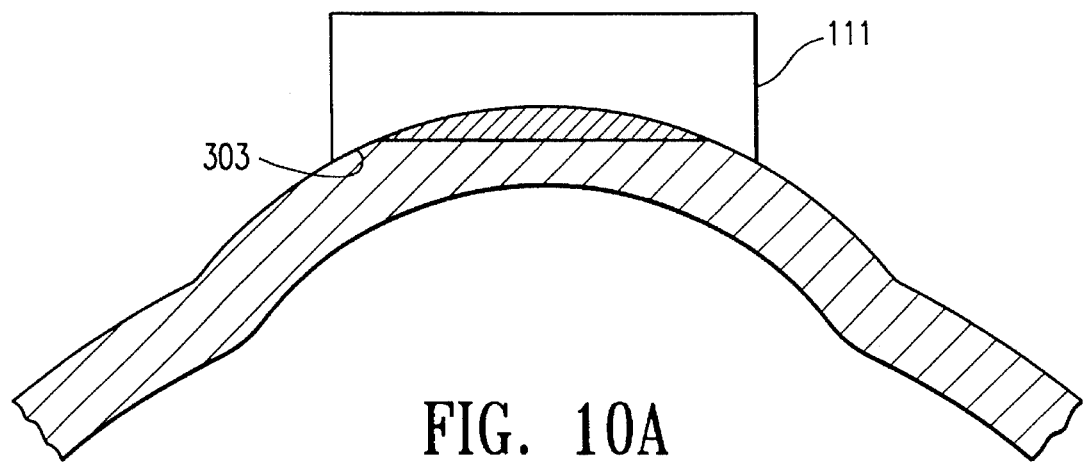
FIG. 10A is a cross-sectional side view of a cornea, showing the present invention in contact with the eye to produce the excision shown in FIG. 10.
Figure 10B:
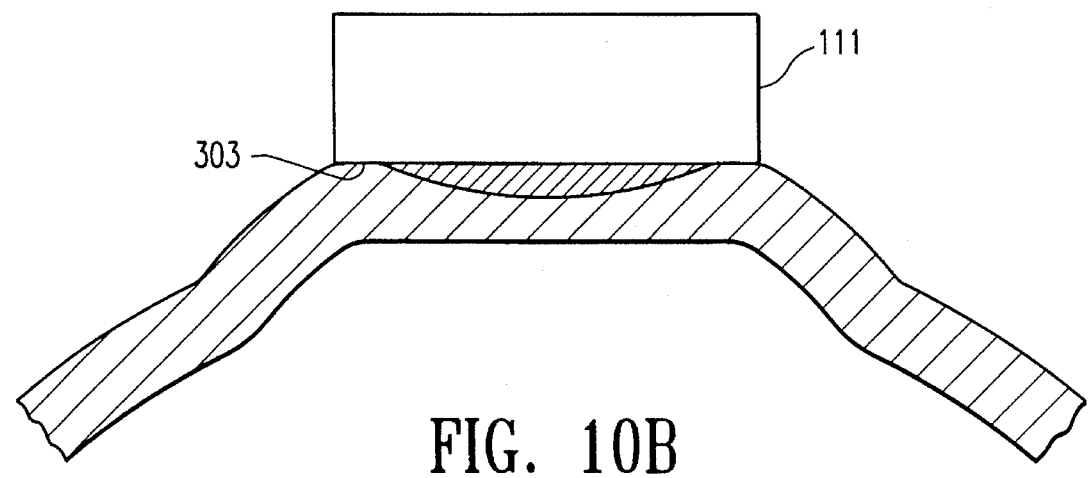
FIG. 10B is a cross-sectional side view of a cornea, showing an alternative embodiment of the present invention in contact with the eye to produce the excision shown in FIG. 10.

For myopia correction, as illustrated in FIG. 10, FIG. 10A, and FIG. 10B, the curvature of the cornea can be reduced by selectively ablating the cornea in such a way that more tissue is removed at the center portion C of the cornea, with a decreasing amount of tissue being removed towards the periphery P of the cornea. The inventive system can also be applied to ablate the corneal tissue near the surface of cornea. The new desired profile of the eye may include Bowman's membrane and part of the stromal layer, depending on the amount of refractive correction required.

As described in co-pending U.S. patent application Ser. No. 07/788,424, the computer control unit 114 provides for the sequence, location, and intensity of laser pulses to be deposited. The deposition pattern is preferably in accordance with the patterns discussed in the section "Method of Depositing Laser Pulses" within the pending application. The applanator plate 111 may have a concave corneal surface 303 as shown in FIG. 10A, or may have a planar corneal surface 303 as shown in FIG. 10B. When the applanator plate 111 has a concave corneal surface 303, the interaction point of the surgical laser beam changes position in only the X-axis and Y-axis. However, when the applanator plate 111 has a planar corneal surface 303, the position of the interaction point of the surgical laser beam is changed in the Z-axis, as well as in the X-axis and Y-axis.

Figure 10C:
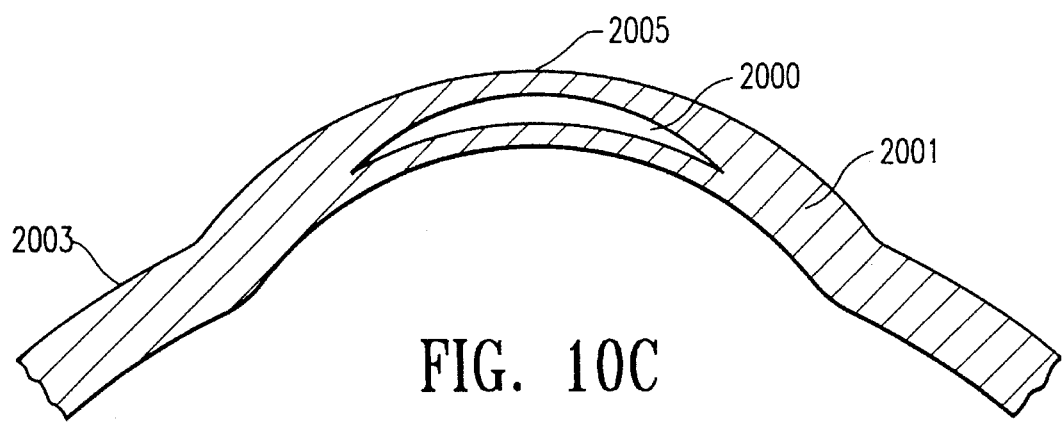
FIG. 10C is a cross-sectional side view of a cornea, showing an excision used to correct moypia.

FIG. 10C illustrates an ablated area 2000 within the stroma 2001 of an eye 2003 without disrupting the surface 2005 of the cornea. An applanator plate 111 having a planar corneal surface 303 is placed in contact with the cornea. The surgical laser beam is directed to ablate a first area of the interior of the stroma at a first fixed distance from the surface of the cornea. After the area has been ablated, the surgical laser beam is directed to a second area of the interior of the stroma adjacent to the first area, and at a second fixed distance from the surface of the cornea. The second distance is less than the first distance, and the second area is smaller than the first area. This procedure is repeated to ablate a predetermined volume defining a cavity. In the preferred embodiment of the present invention, the cavity has a convex-convex shape, more tissue being removed near center of the convex-convex cavity. The depth of the cavity diminishes towards the end of the cavity. The tissue in the ablated volume 2000 is either liquified or vaporized. The liquid or vapor is absorbed by the surrounding unablated tissue. Therefore, the surface of the cornea above the ablated volume 2000 settles down such that the overall curvature of the cornea is reduced. The present invention has the advantage of maintaining a fixed reference with respect to the surface of the cornea, even as corneal tissue is removed by vaporization. Thus, precise ablation of the interior of the stroma is possible.

Figure 10D:
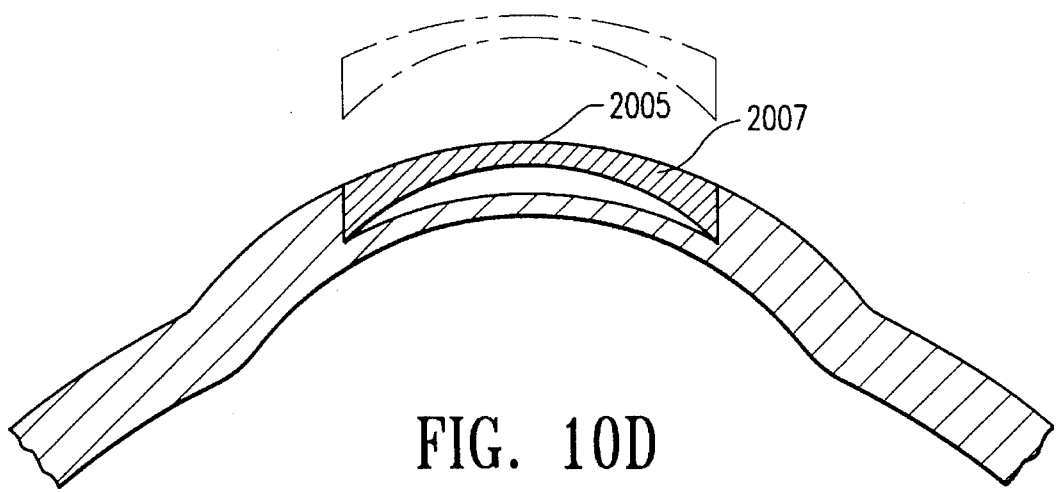
FIG. 10D is a cross-sectional side view of a cornea, showing a portion of the cornea of FIG. 10C removed, and the exposed cornea bed.

In an another embodiment of the present invention, shown in FIG. 10D, a portion 2007 of the cornea is removed after the procedure illustrated in FIG. 10C has been performed. Once the portion 2007 of the cornea has been removed, the portion 2007 is replaced such that that portion 2007 relaxes to conform to the cavity bed resulting in a reduction in the curvature. Such precision is difficult to achieve using an eye-tracking device.

Figure 11:
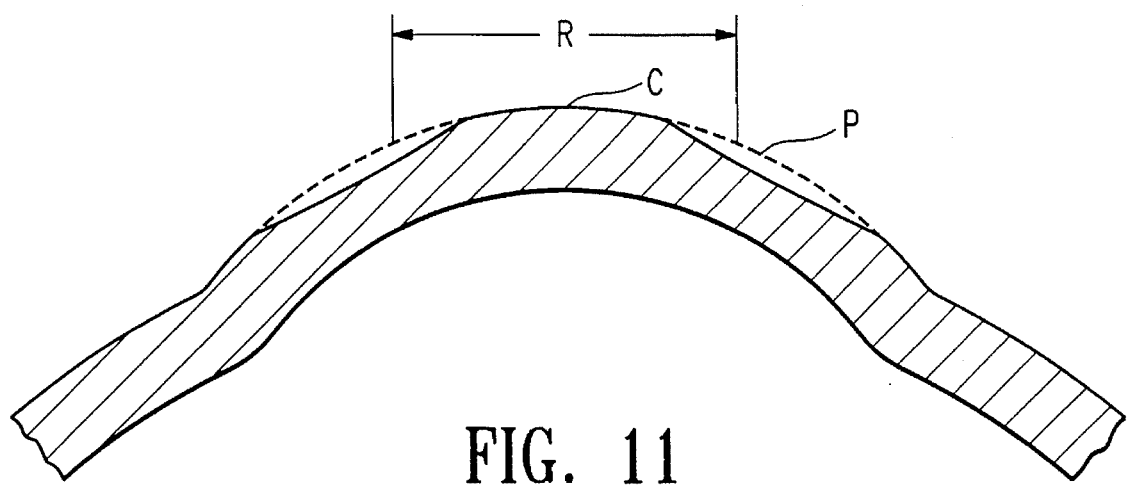
FIG. 11 is a cross-sectional side view of a cornea, showing the use of the present invention to correct hyperopia.
Figure 11A:
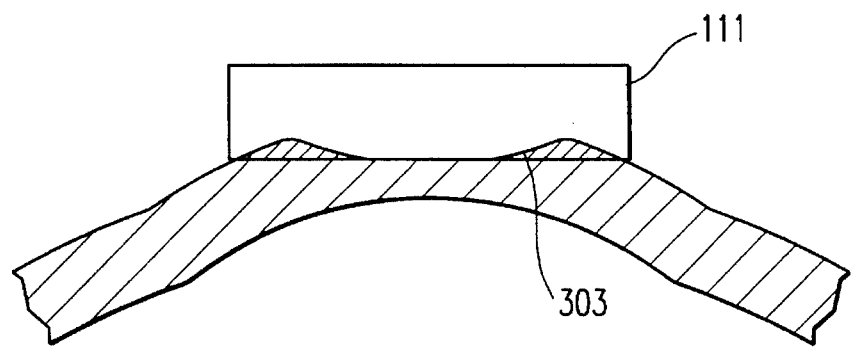
FIG. 11A is a cross-sectional side view of a cornea, showing an applanator plate of the present invention in contact with the eye to produce the excision shown in FIG. 11.
Figure 11B:
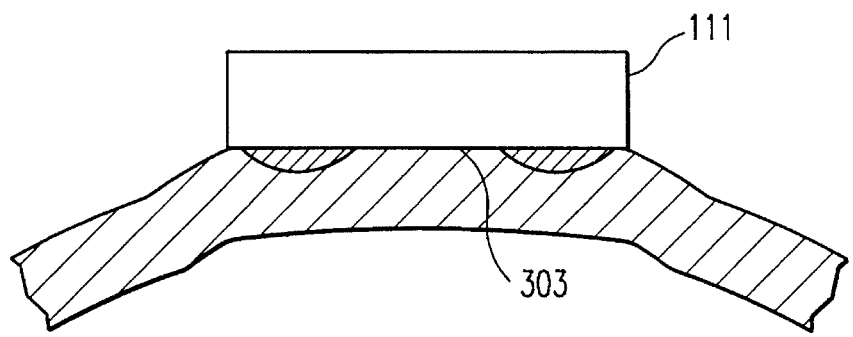
FIG. 11B is a cross-sectional side view of a cornea, showing the applanator plate of the present invention in contact with the eye to produce an excision as shown in FIG. 11.

For hyperopia correction, as illustrated in FIG. 11, the objective is to increase the curvature of the eye. Cornea tissue is to be removed in increasing thickness from the center portion C out towards the periphery P of the cornea. Depending on the amount of correction in the refractive power, the etch gradient for the removed tissue varies. As indicated in FIG. 11, the depth of the removed tissue again decreases near the periphery of the eye for a smooth transition. The size of the usable central region R varies depending on the amount of hyperopic correction. FIG. 11A illustrates the use of an applanator plate having a convex corneal surface 303 used to create the excision shown in FIG. 11. The use of a convex corneal surface 303 allows the excision to be made by controlling the position of the interaction point of the surgical laser beam only in the X-axis and the Y-axis. FIG. 11B illustrates the use of an applanator plate having a planar corneal surface 303.

The invention is particularly useful for the correction of asymmetric refractive errors. Irregular distortions may result from poor matching of a cornea from a transplant, uneven suturing, or from imperfect refractive surgical procedures such as lameliar keratomileusis or epikeratophakia. The inventive system can direct the surgical laser beam to any desired location to sculpt the cornea according to a predetermined shape. The surgical laser beam thus can be applied to smooth out an irregular corneal profile.

Figure 11C:
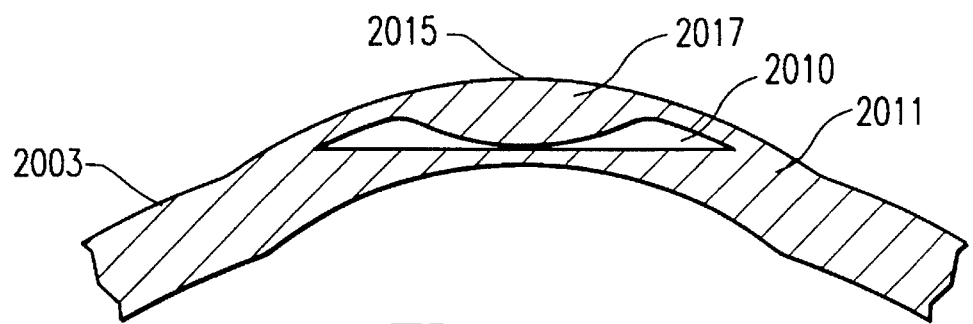
FIG. 11C is a cross-sectional side view of a cornea, showing an excision used to correct hyperopia.

FIG. 11C illustrates an ablated volume 2010 within the stroma 2011 of an eye 2013 without disrupting the surface 2015 of the cornea. An applanator plate 111 having a planar corneal surface 303 is placed in contact with the cornea. The surgical laser beam is directed to ablate a first area of the interior of the stroma at a first fixed distance from the surface of the cornea. After the area has been ablated, the surgical laser beam is directed to a second area of the interior of the stroma adjacent to the first area, and at a second fixed distance from the surface of the cornea. The second distance is donut shaped, with the outside radius of the second area being smaller than the outside radius of the first area. This procedure is repeated to ablate a volume 2010 having a donut shaped cavity. The tissue in the ablated volume 2010 is either liquified or vaporized. The liquid or vapor is absorbed by the surrounding unablated tissue. Therefore, the surface of the cornea above the ablated volume 2010 settles down such that the overall curvature of the cornea is increased.

Figure 10E:
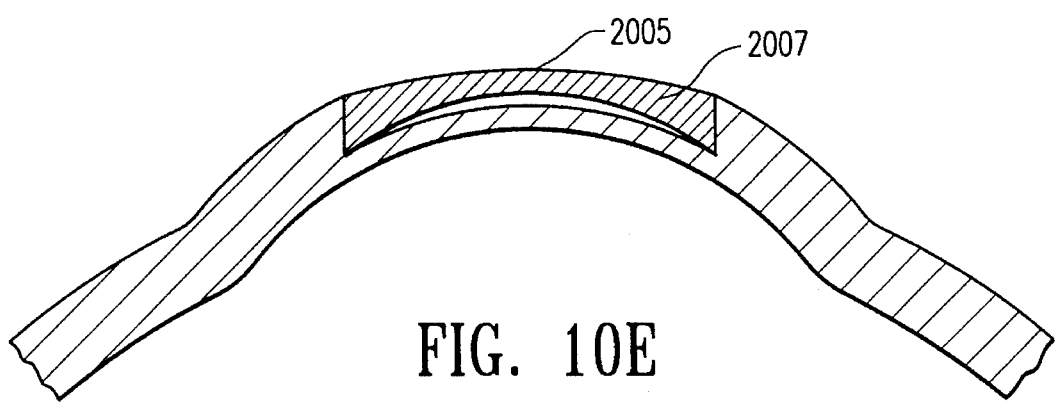
FIG. 10E is a cross-sectional side view of a cornea, showing the portion of the cornea of FIG. 10D replaced in the cornea bed.
Figure 11D:
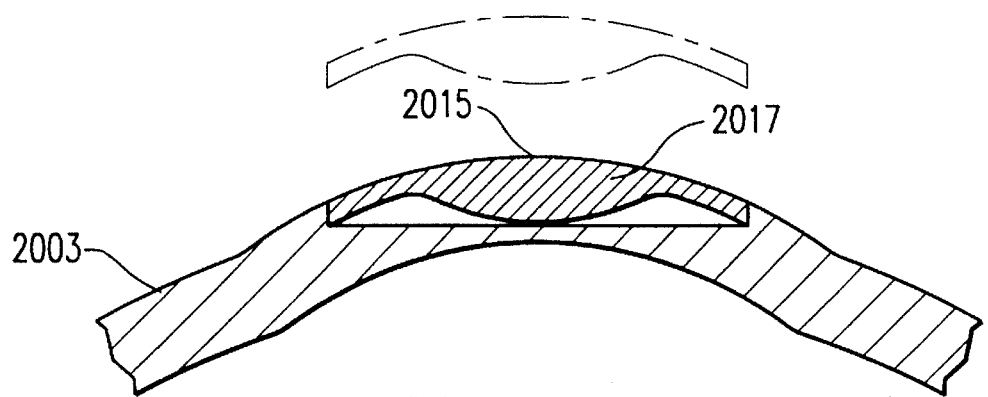
FIG. 11D is a cross-sectional side view of a cornea, showing a portion of the cornea of FIG. 11C removed, and the exposed cornea bed.
Figure 11E:
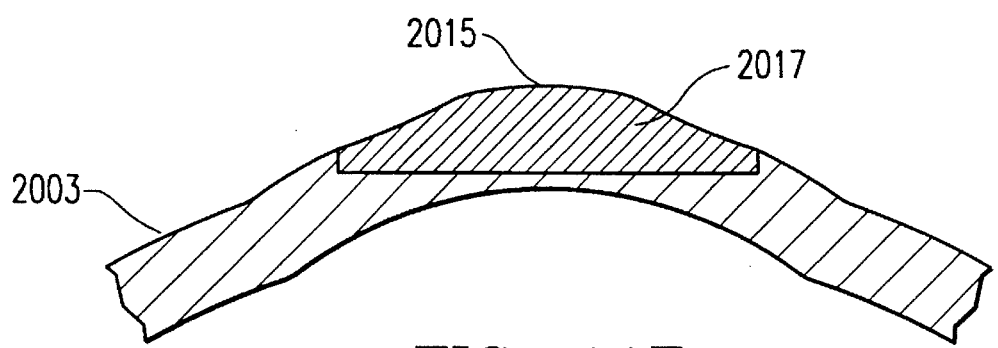
FIG. 11E is a cross-sectional side view of a cornea, showing the surface of the cornea of FIG. 11C replaced in the cornea bed.

In an another embodiment of the present invention, the surface may be removed as described in the discussion of FIGS. 10D and 10E. FIG. 11D illustrates an eye in which the portion 2017 of the cornea is removed after the procedure illustrated in FIG. 11C has been performed. Once the portion 2017 of the cornea has been removed, the portion 2017 is replaced such that that portion 2017 relaxes to conform to the cavity bed resulting in an increase in the curvature. Thus, the surface section 2017 which was removed conforms to the bottom of the cavity formed when the area 2010 of the stroma was ablated. This results in a smooth corneal surface 2015 with an improved radius of curvature.

In addition to the above method for correction of myopia and hyperopia, the above described method may be used to correct regular or irregular astigmatism, or complex refractive errors. The amount and distribution of tissue to be removed from various locations within the stroma is determined by the amount of correction required.

Another use of the invention is to produce standard or custom sculpted cornea caps in advance of need. The invention can be used on a donor cornea or a synthetic cornea substitute to ablate a desired profile to correct for myopia, hyperopia, or astigmatism. Such sculpted caps can then be attached to a properly prepared cornea, in known fashion.

The present invention is also very useful for performing surgical procedures to correct glaucoma by creating a one or more openings through an iris to release fluids from the posterior chamber which create undesirable pressure behind the cornea. In addition, one or more excisions may be created in the posterior or anterior capsule to permit removal of material from the capsule and to implant an interocular lens (IOL) or any other material or structure. Furthermore, portions of the retinal membrane which create tension on the retina may be cut to relieve such tension. Also, portions of the retina may be operated upon to remove harmful tissue. Accordingly, the invention precisely controls and determines the location of the interaction point of a surgical laser beam, and controls the shape of the cornea during ophthalmic surgery. An articulated arm having flexible joints follows any motion of the eye. The applanator plate also provides a means to control the contour of the index of refraction boundary between the corneal epithelium of the eye and the air.

A number of embodiments of the present invention have been described. Nevertheless, it will be understood that various modifications may be made without departing from the spirit and scope of the invention. For example, the surgical laser beam may be delivered to the surgical tip in any manner that permits an exact mapping of the position of the surgical laser beam into a frame of reference fixed to the applanator plate. Thus, a system having a fiber optic path from the surgical laser source to a beam control unit, fixed to the applanator plate, which receives commands from the beam control system within the surgical laser source and accordingly directs the beam through the applanator plate, would fall within the scope of the present invention. Furthermore, any appropriate laser medium may be used in generating the surgical laser beam. Also, any appropriate beam control means may be used.

Accordingly, it is to be understood that the invention is not to be limited by the specific illustrated embodiment, but only by the scope of the appended claims.

I claim:

1. An ophthalmic surgical system for performing surgery upon an eye having an outer surface, the ophthalmic surgical system including:
   a. a laser source for generating a laser beam suitable for ophthalmic surgery;
   b. a controller, optically coupled to the laser beam, for controlling positioning of the laser beam;
   c. a delivery system having a proximal end and a movable distal end, the proximal end being coupled to the laser source for guiding the laser beam to the distal end of the delivery system;
   d. a surgical tip at the distal end of the delivery system for directing the laser beam into an interaction point or tan area having a location, the location of the interaction point being determined by the controller; and
   e. an applanator plate adapted to be rigidly attached to the eye and to the surgical tip, the applanator plate providing a fixed positional reference in three-dimensional space with respect to the laser beam interaction point in the eye to allow three-dimensional control of the interaction point in the eye by the laser source and controller.

2. An ophthalmic surgical system for performing surgery upon an eye having an outer surface, the ophthalmic surgical system including:
   a. a laser source for generating a laser beam suitable for ophthalmic surgery;
   b. a controller, optically coupled to the laser beam, for controlling positioning of the laser beam;
   c. a delivery system having a movable distal end and proximal end, the proximal end being coupled to the laser source, for guiding the laser beam to the distal end of the delivery means;
   d. a surgical tip at the distal end of the delivery system for directing the laser beam into an interaction point or an area having a location, the location of the interaction point being determined by the controller; and
   e. an applanator plate, the a planator plate having at least one shaped surface means, the surgical tip being in contact with the applanator plate during surgery on an eye, the shaped surface means being placed in contact with of the outer surface of the eye during surgery on the eye, the shaped surface means for defining a predetermined area of the eye for a surgical procedure to be performed in such area and for conforming the predetermined area of the eye to the shaped surface of the shaped surface means, such conformed predetermined area providing a positional reference in three-dimensional space with respect to the laser beam interaction point in the eye to allow three-dimensional control of the interaction point in the eye by the laser source and controller, wherein the shaped surface means displaces the outer surface of the eye such that lineal or non-lineal excisions made while the applanator plate is in contact with the eye transform to non-lineal excisions upon removal of the applanator plate from the eye.

3. The ophthalmic surgical system of claim 1 or 2, wherein the applanator plate is made of a material having an index of refraction substantially equivalent to the index of refraction of a cornea of an eye so as to produce essentially no distortion of the laser beam at the boundary between the applanator plate and the outer surface of the eye.

4. The ophthalmic surgical system of claim 1, wherein the delivery system includes an articulated arm means having flexible joints, disposition of which determines a path along which the laser beam propagates from the laser source, for permitting limited motion of the eye with respect to the laser source while preventing the eye from moving with respect to the surgical tip.

5. The ophthalmic surgical system of claim 4, wherein the articulated arm comprises a series of reflective optical elements and lenses positioned to determine the path of the laser beam.

6. The ophthalmic surgical system of claims 1 or 2, wherein the surgical tip includes at least one movable lens, and the location of the interaction point of the laser beam is determined with respect to a three-dimensional positional frame of reference that is fixed relative to the surgical tip by moving at least one lens within the surgical tip.

7. The ophthalmic surgical system of claims 1 or 2, further including an applanator plate retention device, coupled to the applanator plate and configured to be coupled to a scleral-corneal region of the eye, for preventing motion of the applanator plate relative to the eye during eye surgery.

8. The ophthalmic surgical system of claim 7, further including a vacuum generation system, coupled to the applanator plate retention device, for creating a vacuum sufficient to retain the applanator plate retention device motionless relative to the eye.

9. The ophthalmic surgical system of claims 1 or 2, wherein the eye includes a cornea, and the ophthalmic surgical procedure is selected from the group consisting of:

a. radial keratotomy;

b. generating transverse cuts in the cornea;

c. creating straight line excisions in the cornea;

d. creating curved-line excisions in the cornea;

e. creating multiple radial cuts, equal or partially equal in excision length and with an angular separation between cuts, made on the cornea;

f. creating a curved channel excision in the cornea;

g. creating a point excision in the cornea;

h. creating an interrupted line excision in the cornea;

i. creating a curved excision of varying depth in the cornea;

j. removing a geometric area from the cornea;

k. creating a spiral excision in the cornea;

l. creating holes in the posterior capsule of the eye;

m. creating holes in the anterior capsule of the eye;

n. creating holes in an iris of the eye;

o. cutting retinal membranes;

p. producing sculpted cornea caps in advance of need;

q. sculpting the cornea according to a predetermined shape;

r. removing cornea tissue in increasing thickness from the center portion out towards the periphery of the cornea;

s. selectively ablating the cornea in such a way that more tissue is removed at the center portion of the cornea, with a decreasing amount of tissue being removed towards the periphery of the cornea; and t. removing tissue from the eye.

10. The ophthalmic surgical system of claims 1 or 2, wherein at least one shaped surface of the applanator plate is planar.

11. The ophthalmic surgical system of claims 1 or 2, wherein at least one shaped surface of the applanator plate is concave.

12. The ophthalmic surgical system of claims 1 or 2, wherein at least one shaped surface of the applanator plate is convex.

13. The ophthalmic surgical system of claim 1 or 2, wherein at least one shaped surface of the applanator plate is spherical.

14. The ophthalmic surgical system of claims 1 or 2, wherein at least one shaped surface of the applanator plate is aspherical.

15. The ophthalmic surgical system of claim 1, wherein the controller controls the three-dimensional location of the interaction point of the laser beam.

16. The ophthalmic surgical system of claim 15, wherein the beam scanning system includes a lens positioning system for controlling the three-dimensional location of the interaction point of the laser beam.

17. The ophthalmic surgical system of claim 15, wherein the beam scanning system includes at least one galvanometric scanner.

18. The ophthalmic surgical system of claim 15, wherein the beam scanning system includes manual movement of the surgical tip.

19. The ophthalmic surgical system of claim 1, wherein the surgical tip is aged to the applanator plate.

20. An ophthalmic surgical system for performing ophthalmic surgery upon an eye having an outer surface, the ophthalmic surgical system including:

a. a laser source for generating, and controlling positioning of, a laser beam suitable for ophthalmic surgery;

b. a delivery system having a proximal end and a movable distal end, the proximal end being coupled to the laser source, for guiding the laser beam to the distal end of the delivery system;

c. a surgical tip at the distal end of the delivery system, for focussing the laser beam into an area having a size and location, the size and location of the area being determined by the control means of the laser source with respect to a three-dimensional positional frame of refer, race that is fixed relative to the distal end of the delivery system; and an applanator plate, adapted to be rigidly attached to a portion of the outer surface of an eye during surgery, the surgical tip being rigidly attached to the applanator plate during such surgery, the applanator plate thus fixing the three-dimensional positional frame of reference relative to the outer surface of the eye to provide precision three-dimensional reference of an interaction point between tissue of the eye and the laser beam.

21. The ophthalmic surgical system of claim 20, further including a fiber optic path for guiding the laser beam from the laser source to the delivery system.

22. The applanator plate of claim 20, wherein the applanator plate is made of a material having an index of retraction substantially equivalent to the index of refraction of a cornea of a human eye so as to produce essentially no distortion in the laser beam at the boundary between the applanator plate and the outer surface of the eye.

23. The applanator plate of claim 20, further including an applanator plate retention device, coupled to the applanator plate and configured to be coupled to a scleral-corneal region of the eye, for preventing motion of the applanator plate relative to the eye during eye surgery.

24. An applanator plate having a means for fixing the applanator plate to an eye and at least one shaped surface means for contacting and displacing an outer surface of an eye upon which ophthalmic surgery is to be performed, and for conforming the outer surface of the eye to the shape of the contacting shaped surface means, and having a second shaped surface configured to be placed in contact with a tip of a surgical laser instrument having a three-dimensional position, the applanator plate fixing the three-dimensional position of the laser surgical instrument relative to the eye and precisely coupling the laser beam from the laser surgical instrument to selected locations in the eye.

25. The applanator plate of claim 24, wherein at least one of the opposed surfaces is planar.

26. The applanator plate of claim 24, wherein at least one of the opposed surfaces is concave.

27. The applanator plate of claim 24, wherein at least one of the opposed surfaces is convex.

28. The applanator plate of claim 24, wherein at least one of the opposed surfaces is spherical.

29. The applanator plate of claim 24, wherein at least one of the opposed surfaces is aspherical.

30. A method of ophthalmic surgery, including the steps of:

e. generating a laser beam from a laser source;

f. directing the laser beam through at least one optical element from the laser source to a surgical tip;

g. contacting a first surface of an applanator plate to a portion of the outer surface of an eye such that the portion of the outer surface of the eye is displaced to conform to the shape of the first surface of the applanator plate, such contact between the applanator plate and the eye thereby defining an area through which the laser beam interacts with tissue of the eye;

h. rigidly attaching the surgical tip to a second surface of the applanator plate; and i. focusing the laser beam from the surgical tip through the applanator plate to at a plurality of predetermined locations in the eye, each such location having a fixed three-dimensional reference with respect to the applanator plate, the focused laser beam interacting with eye tissue at each such location.

31. The method of ophthalmic surgery in claim 30, wherein the first surface of the applanator plate has one of a plano, aspherical, spherical, concave, or convex shape.

32. The method of ophthalmic surgery in claim 30, wherein the second surface of the applanator plate has one of a plano, aspherical, spherical, concave, or convex shape.

33. The method of ophthalmic surgery in claim 30, further including the step of controlling the three-dimensional location of the laser beam in the eye by means of a beam scanning means.

34. The method of ophthalmic surgery in claim 33, wherein the beam scanning means includes at least one galvanometer drive and at least one mirror.

35. The method of ophthalmic surgery in claim 33, wherein the beam scanning system includes a lens positioning system for controlling the three-dimensional location of the interaction point of the laser beam.

36. The method of ophthalmic surgery in claim 33, wherein the beam scanning system includes manual movement of the surgical tip.

37. The method of ophthalmic surgery in claim 30, wherein the applanator plate is attached to the eye by means of a suction device.

38. The method of ophthalmic surgery in claim 30, further including the step of directing the laser beam by means of an articulated arm defining an optical path from the laser source to the surgical tip.

39. The method of ophthalmic surgery in claim 30, further including the step of directing the laser beam by means of a fiber optic path from the laser source to the surgical tip.

40. The method of ophthalmic surgery in claim 30, wherein the interaction of the laser beam with eye tissue includes ablation of eye tissue.

41. The method of ophthalmic surgery in claim 30, further including the steps of:

a. focussing the laser beam at a location in the eye, such location including at least one of the anterior or the posterior capsule of the eye, the lens of the eye, or the retina of the eye;

b. excising eye tissue at the focus location with the laser beam; and c. scanning the location of the focussed laser beam along a predetermined direction, over a predetermined area, or inside a predetermined volume inside the eye.

42. The method of ophthalmic surgery in claim 30, wherein the interaction of the laser beam with eye tissue includes heating eye tissue.

43. The method of ophthalmic surgery in claim 30, further including the steps of:

a. focussing the laser beam at a location in the eye, such location including at least one of the anterior or the posterior capsule of the eye, the lens of the eye, or the retina of the eye;

b. heating eye tissue at the focus location with the laser beam; and c. scanning the location of the focussed laser beam along a predetermined direction, over a predetermined area, or inside a predetermined volume inside the eye.

44. The method of ophthalmic surgery in claim 30, wherein the interaction of the focussed laser beam with eye tissue attains an objective of changing the refractive power of the eye by the steps of:

a. locating the focussed laser beam at one of the epithelium, Bowman's layer, or stroma of the eye;

b. excising eye tissue at the focus location with the laser beam; and c. scanning the location of the focussed beam along a predetermined direction, over a predetermined area, or inside a predetermined volume of the eye.

45. The method of ophthalmic surgery in claim 44, wherein the excised tissue volume is on the outer surface of the cornea of the eye.

46. The method of ophthalmic surgery in claim 44, wherein the excised tissue volume is inside the cornea of the eye.

47. The method of ophthalmic surgery in claim 46, wherein the excised tissue volume comprises a cavity, and further including the step of collapsing the cavity to change the curvature of the portion of the outer surface of the eye.

48. The method of ophthalmic surgery in claim 47, further including the step of collapsing the cavity by compressing the outer surface of the cornea with the applanator plate.

49. The method of ophthalmic surgery in claim 44, wherein the objective is to correct myopia conditions, and further includes the step of excising a tissue volume in the eye which has a shape substantially equivalent to a positive lens, with the intended optical axes of such lens shape being aligned along the visual axes of the eye; thereby flattening the curvature of the portion of the outer surface of the eye.

50. The method of ophthalmic surgery in claim 44, wherein the objective is to correct hyperopia conditions, and further includes the step of excising a tissue volume in the eye which has a shape substantially equivalent to a negative lens with an outer periphery tapered to essentially a zero thickness, with the intended optical axes of such lens shape being aligned along the visual axes of the eye, thereby steepening the curvature of the portion of the outer surface of the eye.

51. The method of ophthalmic surgery in claim 44, wherein the objective is to perform a procedure to correct the refractive power, further including the steps of:

f. contacting an applanator plate having a first surface of a predetermined concave curvature to the portion of the outer surface of the eye, thereby displacing the surface of the eye to conform the portion of the outer surface of the eye to the same curvature;

g. applying the focused laser beam to the eye; and h. excising eye tissue on one or more planes at a predetermined angle with respect to the visual axes of the eye, such that the excision separates a layer of eye tissue defined by the planes and the first surface of the applanator plate.

52. The method of ophthalmic surgery in claim 51, wherein the separated tissue layer has the shape substantially equivalent to a plano lens with predetermined area and thickness.

53. The method of ophthalmic surgery in claim 51, wherein the separated tissue layer has the shape substantially equivalent to a positive lens with predetermined area and thickness.

54. The method of ophthalmic surgery in claim 51, wherein the separated tissue layer has the shape substantially equivalent to a negative lens with predetermined area and thickness.

55. The method of ophthalmic surgery in claim 51, further including the steps of:

a. removing the separated layer of eye tissue;

b. ablating the stroma bed of the eye to remove a tissue volume essentially in the shape of a plano lens of any predetermined profile;

c. replacing the separated layer of eye tissue such that the curvature of the portion of the outer surface of the eye is modified.

56. The method of ophthalmic surgery in claim 51, further including the steps of:

a. removing the separated layer of eye tissue;

b. ablating the stroma bed of the eye to remove tissue volume essentially in the shape of a positive lens;

c. replacing the separated layer of eye tissue such that the curvature of the portion of the outer surface of the eye is modified.

57. The method of ophthalmic surgery in claim 51, further including the steps of:

a. removing the separated layer of eye tissue;

b. ablating the stroma bed of the eye to remove tissue volume essentially in the shape of a negative lens;

c. replacing the separated layer of eye tissue such that the curvature of the portion of the outer surface of the eye is modified.

58. The method of ophthalmic surgery in claim 51, further including the steps of:

a. removing the separated layer of eye tissue;

b. ablating the posterior surface of the separated layer of eye tissue to remove a tissue volume essentially in the shape of a plano lens;

c. replacing the separated layer of eye tissue, such that the curvature of the portion of the outer surface of the eye is modified.

59. The method of ophthalmic surgery in claim 51, further including the steps of:

a. removing the separated layer of eye tissue;

b. ablating the posterior surface of the separated layer of eye tissue to remove a tissue volume essentially in the shape of a positive lens;

c. replacing the separated layer of eye tissue, such that the curvature of the portion of the outer surface of the eye is modified.

60. The method of ophthalmic surgery in claim 51, further including the steps of:

a. removing the separated layer of eye tissue;

b. ablating the posterior surface of the separated layer of eye tissue to remove a tissue volume essentially in the shape of a negative lens;

c. replacing the separated layer of eye tissue, such that the curvature of the portion of the outer surface of the eye is modified.

61. The method of ophthalmic surgery in claim 30, wherein the ophthalmic surgical procedure is selected from the group consisting of:

a. radial keratotomy;

b. generating transverse cuts in the cornea;

c. creating straight line excisions in the cornea;

d. creating curved-line excisions in the cornea;

e. creating multiple radial cuts, equal or partially equal in excision length and with an angular separation between cuts, made on the cornea;

f. creating a curved channel excision in the cornea;

g. creating a point excision in the cornea;

h. creating an interrupted line excision in the cornea;

i. creating a curved excision of varying depth in the cornea;

j. removing a geometric area from the cornea;

k. creating a spiral excision in the cornea;

l. creating holes in the posterior capsule of the eye;

m. creating holes in the anterior capsule of the eye;

n. creating holes in an iris of the eye;

o. cutting retinal membranes;

p. producing sculpted cornea caps in advance of need;

q. sculpting the cornea according to a predetermined shape;

r. removing cornea tissue in increasing thickness from the center portion out towards the periphery of the cornea;

s. selectively ablating the cornea in such a way that more tissue is removed at the center portion of the cornea, with a decreasing amount of tissue being removed towards the periphery of the cornea; and t. removing tissue from the eye.

\* \* \* \* \*

UNITED STATES PATENT AND TRADEMARK OFFICE
CERTIFICATE OF CORRECTION

PATENT NO. : 5,549,632
DATED : August 27, 1996
INVENTOR(S) : Shui T. Lai

It is certified that error appears in the above-identified patent and that said Letters Patent is hereby corrected as shown below:

On the title page, item [73] Assignee, delete "Novatec Laser Systems, Inc.".

Signed and Sealed this

Eleventh Day of April, 2000

Q. TODD DICKINSON

*Attest:*

*Attesting Officer*     *Director of Patents and Trademarks*